US006503205B2

(12) United States Patent
Manor et al.

(10) Patent No.: US 6,503,205 B2
(45) Date of Patent: Jan. 7, 2003

(54) DUAL ULTRASONIC TRANSDUCER PROBE FOR BLOOD FLOW MEASUREMENT, AND BLOOD VESSEL DIAMETER DETERMINATION METHOD

(75) Inventors: Dan Manor, Kadima (IL); Eli Levy, Raanana (IL); Roni Bibi, Herzelia (IL); Sergei Lukaschuk, Ra'anana (IL)

(73) Assignee: Cardiosonix Ltd., Raanana (IL)

( * ) Notice: Subject to any disclaimer, the term of this patent is extended or adjusted under 35 U.S.C. 154(b) by 0 days.

(21) Appl. No.: 09/859,672

(22) Filed: May 18, 2001

(65) Prior Publication Data

US 2002/0042574 A1 Apr. 11, 2002

Related U.S. Application Data

(63) Continuation-in-part of application No. PCT/IL99/00620, filed on Nov. 18, 1999.

(30) Foreign Application Priority Data

Nov. 18, 1998 (IL) ................................. 127112

(51) Int. Cl.[7] .............................................. A61B 8/00
(52) U.S. Cl. ...................................................... 600/459
(58) Field of Search .................................. 600/459, 460, 600/458, 439, 461, 455, 454

(56) References Cited

U.S. PATENT DOCUMENTS

| 4,103,679 | A |   | 8/1978  | Aronson         |         |
|-----------|---|---|---------|-----------------|---------|
| 4,370,985 | A |   | 2/1983  | Takeichi et al. |         |
| 5,701,898 | A | * | 12/1997 | Adam et al.     | 600/459 |
| 6,171,248 | B1| * | 1/2001  | Hossack et al.  | 600/459 |
| 6,186,951 | B1| * | 2/2001  | Lizzi et al.    | 600/458 |
| 6,261,233 | B1| * | 7/2001  | Kantorovich     | 600/454 |

FOREIGN PATENT DOCUMENTS

WO            97 24986        7/1997

OTHER PUBLICATIONS

Fox, "A Closed Form Solution to the Doppler Velocity Equation", *Annual Northeast Bioengineering Conf.*, pp. 181–184, Mar. 14–15, 1985.

Tortoli et al., "An ultrasonic Doppler Flowmeter for medical application", *Alta Frequenza,* (1985), vol. 54, No. 5, pp. 312–315.

Sklandany et al., "New, Angle–independent, Low–Cost Doppler System to Measure Blood Flow", *The American Journal of Surgery,* (1998), vol. 176, pp. 179–182.

esp@cenet.com, Abstract, Meister, "Process and device for determining the speed and the rate of flow of a fluid in a pipe by using a Doppler echographic method", publication No. EP0150672, Publication Date Aug. 7, 1985.

* cited by examiner

Primary Examiner—Francis J. Jaworski
Assistant Examiner—Maulin Patel
(74) Attorney, Agent, or Firm—Browdy and Neimark

(57) ABSTRACT

A dual ultrasonic transducer probe and a method of utilizing the probe to determine a blood vessel diameter are presented. The probe comprises first and second ultrasound transducers whose ultrasound beams intercept at an acute angle, and which can be so disposed relative to a blood vessel's longitudinal axis that both their ultrasound beam axes intercept the blood vessel's longitudinal axis. The blood vessel diameter determination method is based on the creation of a two-dimensional matrix of complex reflection amplitude values for each of the beams along an axis of its propagation.

28 Claims, 12 Drawing Sheets

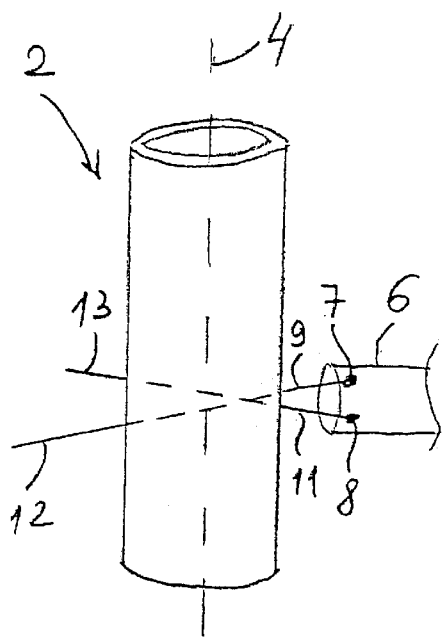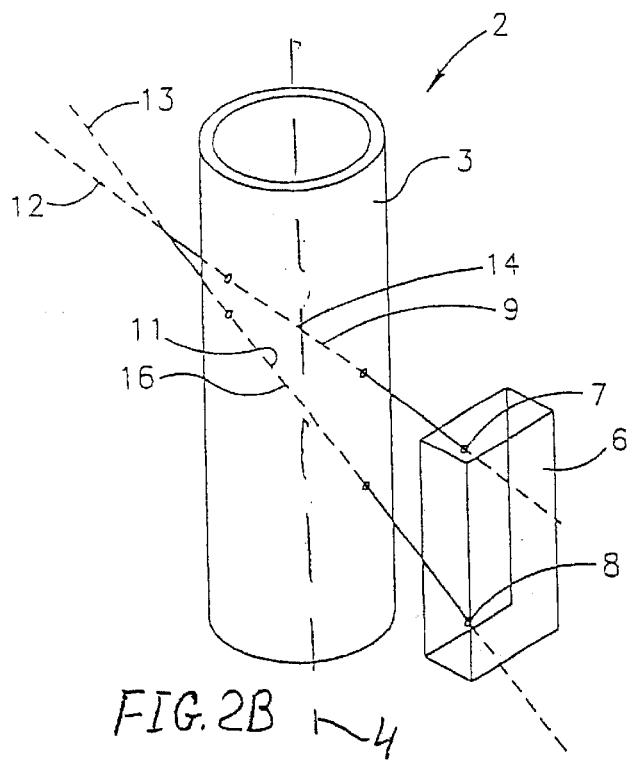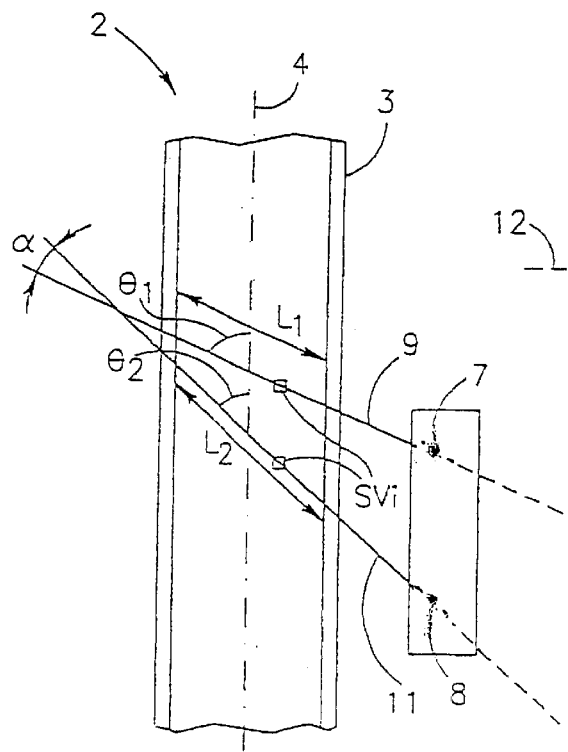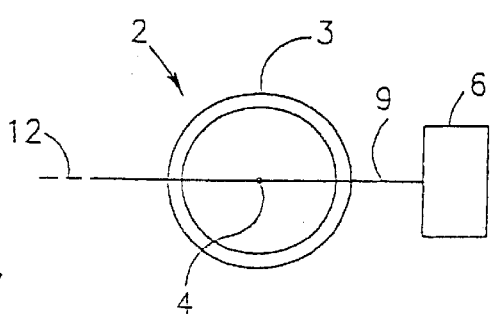
FIG. 2A
FIG. 2B
FIG. 2C
FIG. 2D

DUAL ULTRASONIC TRANSDUCER PROBE FOR BLOOD FLOW MEASUREMENT, AND BLOOD VESSEL DIAMETER DETERMINATION METHOD

FIELD OF THE INVENTION

The invention relates to a dual ultrasonic transducer probe for use in a Doppler based ultrasound system for blood flow measurement and determination of associated hemodynamic parameters, and a blood vessel diameter determination method.

BACKGROUND OF THE INVENTION

U.S. Pat. No. 4,370,985 discloses a Doppler based ultrasound probe device for measuring a blood flow rate and a blood vessel diameter. This technique is based on the continuous transmission of ultrasonic waves.

EP 0150672 discloses a process and device for determining the velocity and rate of flow of a fluid in a pipe by using a Doppler echographic method. Here, two mutually attached wave-train transmitter-receiver units are used and oriented with respect to a pipe such that the axis of one of the units is perpendicular to the axis of the pipe. According to this technique, the transit time between the transmission of a wave train by this transmitter-receiver unit and the reception of the reflected train is measured for calculating the diameter and perpendicular cross-section of the pipe.

In U.S. Pat. No. 4,103,679 to Aronson, there is illustrated and described a Doppler based ultrasound system for blood flow measurement in a blood vessel which requires that an ultrasound transducer array be so disposed relative to the blood vessel's longitudinal axis that a Pulse Wave ultrasound beam emanating therefrom intercepts the blood vessel's longitudinal axis at a variable beam inclination angle $\theta$, whereby blood flow measurement can be quantitatively measured independent of the beam inclination angle.

An article entitled *"New, Angle-independent, Low-Cost Doppler System to Measure Blood Flow"* by M. Skladany et al., The American Journal of Surgery, Volume 176, August 1998, pgs. 179–182, illustrates and describes a similar Doppler based ultrasound system for blood flow measurement.

Another technique based on the transmission of pulses of two ultrasound waves aimed at determining the blood velocity is disclosed in WO 97/24986. This technique is based on the zero-crossing method for frequency measurement of Doppler shifts and the use of FM modulated or pulse signals with range clipping for localizing velocity measurements.

However, the aforementioned references neither address the practical difficulties involved with ensuring that an ultrasound beam is correctly positioned with respect to a blood vessel's longitudinal axis, nor the accurate measurement of a blood vessel's diameter, both factors playing a major role in an accurate blood flow measurement determination.

SUMMARY OF THE INVENTION

There is accordingly a need in the art to facilitate measurements of a blood vessel diameter, as well as a blood flow and velocity profile at the blood vessel axis, by providing a novel dual ultrasonic transducer probe and a method of blood vessel diameter measurement utilizing a pair of ultrasound beams.

The main idea of the present invention consists of the following. Two transducers in the probe should be oriented with respect to each other such that ultrasound beams generated by the transducers define beam propagation axes intercepting at a certain acute angle. The transducers should be desirably positioned with respect to the blood vessel under measurements, namely such that each of the beam propagation axes intercept the longitudinal axis of the blood vessel. This can be implemented by displacing the transducers with respect to the blood vessel (either manually or by means of a specifically designed support assembly) and performing preliminary measurements of the blood vessel diameter.

According to the invented method, once the probe is desirably positioned, measurements are carried out consisting of insonating the blood vessel with two pulse-wave ultrasound beams, in a manner to substantially simultaneously (in comparison to the physiological time scale) obtain multiple sample volumes at successive coordinates (gates) all along each of the beam propagation axis. In other words, for each of the beams an amplitude vector of the reflections with Doppler shifted frequencies is obtained as an n-element vector. By applying the complex demodulation technique, which utilizes the synchronous multiplication of the input real vector of reflection amplitudes on two periodic functions with 90°-shift in phase, and a low pass filtering, the n-element vector of complex values (I & Q) for each of the beam is obtained. By this, the central frequency of the complex vector is shifted from that of the ultrasound pulse towards zero frequency. By repeating the ultrasound pulses transmission/receiving procedure m times, an n×m two-dimensional matrix $E_{ij}$ of reflection amplitude values is obtained for each of the beams. Here, i is the gate coordinate index (i=1, . . . , n) and j is the time coordinate index (j=1, . . . , m). It should be understood that each of the reflection amplitude values is complex and is indicative of the amplitude and the phase of the reflection at the respective gate at a certain time. By processing and analyzing these matrices (for two beams), the diameter of the blood vessel can be calculated, as well as dynamic characteristics of the blood flow, such as Doppler shifts, inclination angles, velocity, and velocity profile along the ultrasound beam.

The present invention actually enables for automatic location of the central axis of the blood vessel. Therefore, by measuring the time variations of the detected reflection at this location, and calculating blood flow velocity values, the velocity profile at the central cross section of the blood vessel along the ultrasound beam can be determined.

Thus, in accordance with a first aspect of the present invention, there is provided a dual ultrasonic transducer probe for use in a Doppler based ultrasound system for blood flow measurement, the probe comprising: a housing containing first and second ultrasound transducers each operable in transmitting and receiving modes, the transducers producing first and second ultrasound beams propagating along first and second beam propagation axes, the first and second transducers being oriented with respect to each other such that the first and second beam propagation axes intersect at a certain acute angle, and being displaceable with respect to a patient's blood vessel to enable desired positioning of the probe such that each of the first and second beam propagation axes intersect a longitudinal axis of the blood vessel, which is determined by performing a preliminary measurement of a diameter of the blood vessel.

The housing may be of an elongated shape, the first and second transducers being mounted at a distal end of the housing. By the manual displacement of the housing with real-time analysis of the preliminary measurements, the desired positioning of the probe can be provided.

Alternatively, a specific support assembly may be used for the probe positioning. The support assembly is rotatable about the first beam propagation axis, whereby the second ultrasound transducer rotates about the first beam propagation axis. The support assembly is displaceably mounted in the housing for displacing the first and second ultrasound transducers in tandem. The arrangement is such that both the first and second beam propagation axes intercept the blood vessel's longitudinal axis and correspondingly subtend acute beam inclination angles $\theta_1$ and $\theta_2$ therewith for enabling the measurement of Doppler shift frequencies along said first and second beam propagation axes. Such a probe facilitates manipulation of its ultrasonic transducers relative to a blood vessel such that both their ultrasonic beam axes intercept the blood vessel's longitudinal axis, and subtend acute beam inclination angles therewith. Typically, such positioning is a two step process including a first step for intercepting the blood vessel's longitudinal axis with the first ultrasonic beam; and a second step for intercepting the blood vessel's longitudinal axis with the second ultrasonic beam by rotating it relative to the first ultrasonic beam which is maintained in its intercepting position. The present invention is particularly suitable for accurate blood flow measurement in a human subject's carotid artery.

In accordance with a second aspect of the present invention, there is provided a blood vessel diameter determination method comprising the steps of:

(a) providing a desired positioning of first and second ultrasound transducers relative to the blood vessel to ensure that each of first and second ultrasound beam propagation axes intercepts the blood vessel's longitudinal axis and subtends, the transducers being oriented with respect to each other such that the first and second beam propagation axes are interceptable at an acute angle, the desired positioning being provided by displacing the transducers with respect to the blood vessel and performing preliminary measurements of the blood vessel diameter;

(b) carrying out measurements to determine the blood vessel diameter by energizing the first and second ultrasound transducers to insonate the blood vessel with first and second pulsed wave ultrasound beams, respectively, and receiving an amplitude vector of reflections with Doppler shifted frequencies for each of the ultrasound beams, wherein said amplitude vector of reflections is an n-element vector formed by complex values of the amplitudes from n successive coordinates along the ultrasound beam vector representing n successive gates;

(c) repeating step (b) m times and obtaining an n×m two-dimensional matrix of the reflection amplitudes $E_{ij}$, wherein i is the gate coordinate along the beam axis, i=1, . . . , n, and j is the time coordinate, j=1, . . . , m, each of the reflection amplitude values being complex and being representative of the amplitude and phase of the reflection at the respective gate at a certain time; and (d) processing said matrix to calculate the blood vessel diameter.

The preliminary measurements ensure that the axes of the beams intercept with the longitudinal axis of the blood vessel, and include measurements of the blood vessel diameter associated with the first and second beams, respectively. The probe is displaced with respect to the blood vessel until equal and maximal values of diameters are measured for both beams. Additionally, in the center region of the blood vessel (at the location of interception between the beam and the vessel axes), the blood flow velocity values measured by the two beams have maximal and equal values.

The processing of the matrix consists of the following. A high pass filtering is applied to the matrix of the reflection amplitude values $E_{ij}$ along j-coordinate to remove values relating to a low frequency part of a detected signal. By this, the reflection signal associated with blood vessel walls is removed. A filtered matrix of the reflection amplitude values for each of the beams is processed to calculate an n-element real vector of time averaged amplitudes $E_i$ along the beam propagation axis. The calculated real vector is analyzed for each of the beams to determine a beam corrected chord length L of a portion of the ultrasound beam extending between an outermost surface $S_O$ and an innermost surface $S_I$ of the blood vessel's wall correspondingly adjacent the ultrasound transducer, and remote therefrom. The corrected chord length L and a beam inclination angle for each of the beams are utilized to calculate the blood vessel diameter D. Generally, the beam inclination could be calculated in the conventional manner, namely, from the ratio of Doppler shift frequencies in both ultrasound beams measured at the center of the blood vessel.

The blood vessel diameter determination method of the present invention can be implemented using either one of two approaches for calculating the n-element real vector of reflection amplitude values $E_i$ along the ultrasound beam axis, and either one of two approaches for determining the portion of the ultrasound beam which intercepts the blood vessel's wall.

The two approaches for calculating the n-element real vector $E_i$ are based on either time or frequency domain operations on the (n×m) two dimensional matrix of reflection amplitude values $E_{ij}$. The two approaches for determining the portion of the ultrasound beam which intercepts the blood vessel's wall are based on parametric estimation for detecting initial and final parabolic like portions along the n-element vector $E_i$, and thresholding techniques. Due to the inclination of the ultrasound beam relative to the blood vessel, the beam corrected chord length L is preferably calculated according to the relationship: L=P−B/tan θ, where P is a measured chord length, and B is the beam width of the ultrasound beam.

Additionally, the processing and analyzing of the matrix $E_{ij}$ provides for determining the inclination angles for the beams and determining the blood velocities in successive locations along the beams' axes. This allows for creating the velocity profile, and therefore calculating the blood flow rate. Considering the velocity profile across the vessel as being symmetric about the longitudinal axis of the vessel, the blood flow rate F could be calculated as:

$$F = 2\pi \cdot \int_0^R V(r) \cdot r \cdot dr$$

where R is the radius of the blood vessel, r is a radial coordinate measured from the center of the vessel, and V(r) is the radial velocity dependence. If the probe is positioned correctly, then the points corresponding to the center of chords $L_1$ and $L_2$ are located on the axis of the blood vessel, and the coordinate of the vessel center is determined for both ultrasound beams. The velocity values measured at the center of the blood vessel in both beams should be equal after averaging the detected signals over time. This analysis could be used in addition to the equal-and-maximum diameters criteria to verify the probe positioning. The use of the vessel center coordinate is also needed to display the time dependence of velocity (or Doppler frequency) in the vessel. At the preliminary stage of the probe positioning, the Doppler signal from the center of chords $L_1$ or $L_2$ appears on the display to help in finding initial probe position.

BRIEF DESCRIPTION OF THE DRAWINGS

For a better understanding of the present invention and to show how the same can be carried out in practice, by way of non-limiting examples, reference will be made to the accompanying drawings, in which:

FIGS. 2A and 2B are schematic representations of the disposition of the probe's ultrasound transducers relative to the subject's carotid artery during blood flow measurement, showing two possible orientations of the beam propagation axes with respect to the central axis of the blood vessel, respectively;

FIGS. 2C and 2D are respectively side and top views of the blood vessel irradiated by the beams of either of FIGS. 2A and 2B;

DETAILED DESCRIPTION OF THE DRAWINGS

Figure 1:
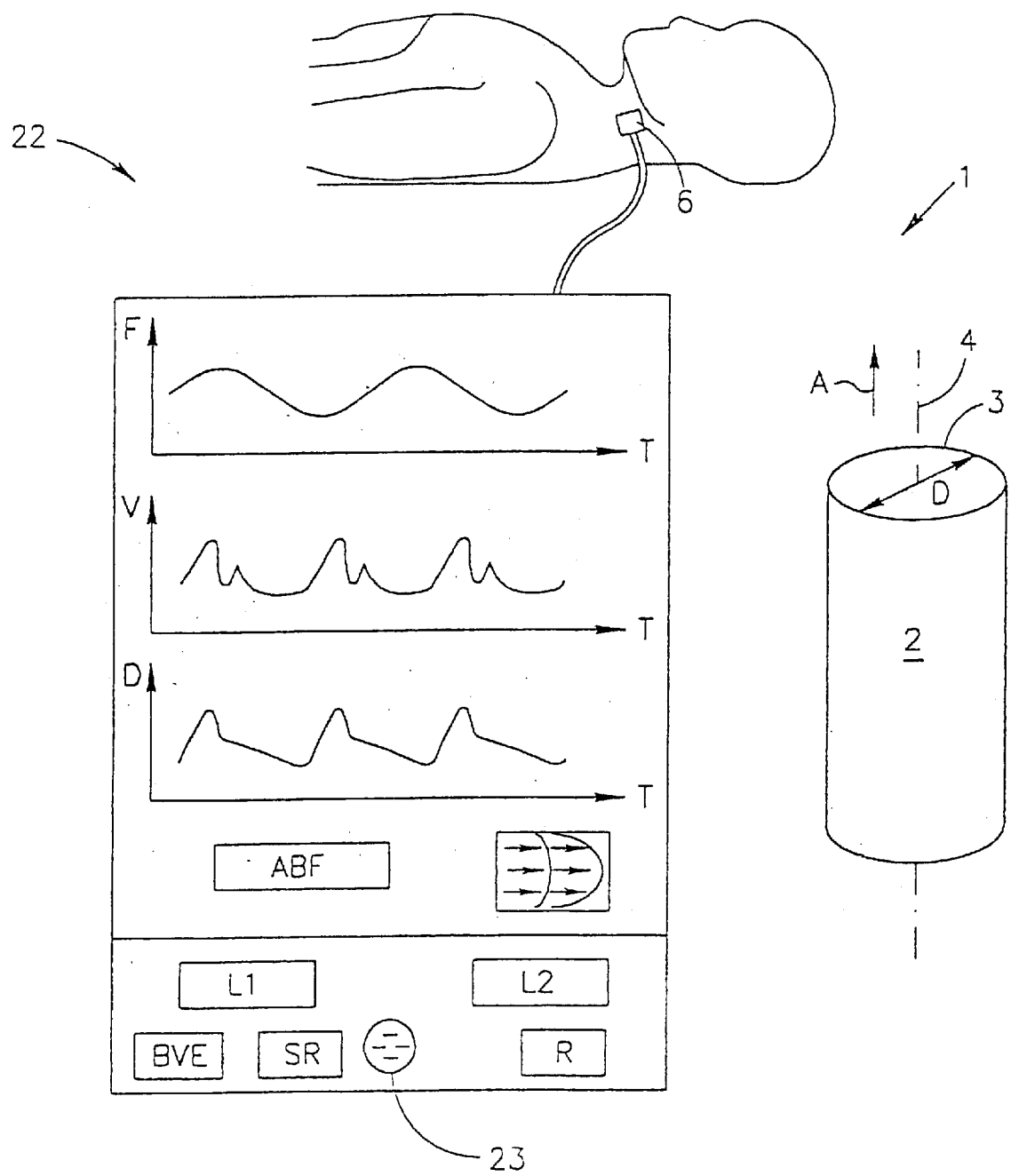
FIG. 1 is a pictorial representation showing a system of the present invention for blood flow measurement in a human subject's carotid artery including a dual ultrasound transducer probe, and a schematic representation of his carotid artery.

With reference now to FIG. 1, there is shown a system 1 for blood flow measurement in a subject's artery, and the determination of associated hemodynamic parameters. The subject's carotid artery is schematically shown as a right cylindrical duct 2 with a sidewall 3, a longitudinal axis 4, a diameter D, and through which blood flows in a direction denoted A. The system includes an ultrasonic probe 6 to be applied to the patient. In the present example, the probe is applied to the patient's carotid artery.

Referring to FIGS. 2A–2D, there are shown the main components of the probe 6 and their orientation with respect to the blood vessel under measurements. The probe 6 has an elongated shape and comprises a pair of ultrasound transducers 7 and 8 mounted at the distal end of the probe for transmitting and receiving, respectively, a pair of narrow Pulse Wave (PW) multi-gated ultrasound beams 9 and 11 having a pair of ultrasound beam axes 12 and 13 which intercept at an acute intersection angle α.

It should be understood that, according to the present invention, the transducers 7 and 8 are oriented with respect to each other and with respect to the blood vessel so as to ensure that each of the beam propagation axes 12 and 13 crosses the central axis 4 of the blood vessel. It means that the beams' axes and the longitudinal axis of the blood vessel lie in a common plane. To this end, the transducers are oriented such that the axes of the ultrasound beams forms a certain angle with respect to each other, and appropriate displacement either of both transducers together (i.e., the entire probe) or one transducer with respect to each other is provided.

FIGS. 2A and 2B illustrate two possible probe designs with different orientations of the ultrasound beam axes with respect to the blood vessel. As better seen in FIGS. 2C and 2D, the beam propagation axes 12 and 13 cross the central axis 4 of the blood vessel. It should be noted that the correct positioning of the transducers with respect to the blood vessel may be achieved by the manual manipulation of the probe with respect to the patient's artery and analysis of the measured diameters and Doppler signals enables to correctly position the probe. Alternatively, a specific support assembly can be used, as described below with respect to FIGS. 4–10. It should be noted that the configurations of FIGS. 2A and 2B are different with respect to an algorithm of the velocity and inclination angles measurements, but are similar with respect to the purposes of the present invention, i.e., an algorithm of the boundaries detection (diameter measurements). For both beam propagation configurations, the axes 12 and 13 of the multi-gated ultrasound beams 9 and 11 intercept at an acute intersection angle α, and intercept the central axis 4 of the blood vessel at angles $\theta_1$ and $\theta_2$.

The ultrasound transducers 7 and 8 can be moved in tandem, and the ultrasound transducer 8 can be rotated about the so-called fixed ultrasound beam axis 12 such that the directions of their ultrasound beams 9 and 11 can be readily manipulated to intercept the carotid artery's longitudinal axis 4. On such positioning, the ultrasound beams 9 and 11 subtend acute beam inclination angles $\theta_1$ and $\theta_2$ where $\theta_1=\theta_2+\alpha$ with the carotid artery's longitudinal axis 4, respectively, and have beam portions 14 and 16 (shown in hashed lines in FIG. 2A) of lengths $L_1$ and $L_2$, respectively, which transverse the carotid artery at diametrically opposite portions.

Figure 3:
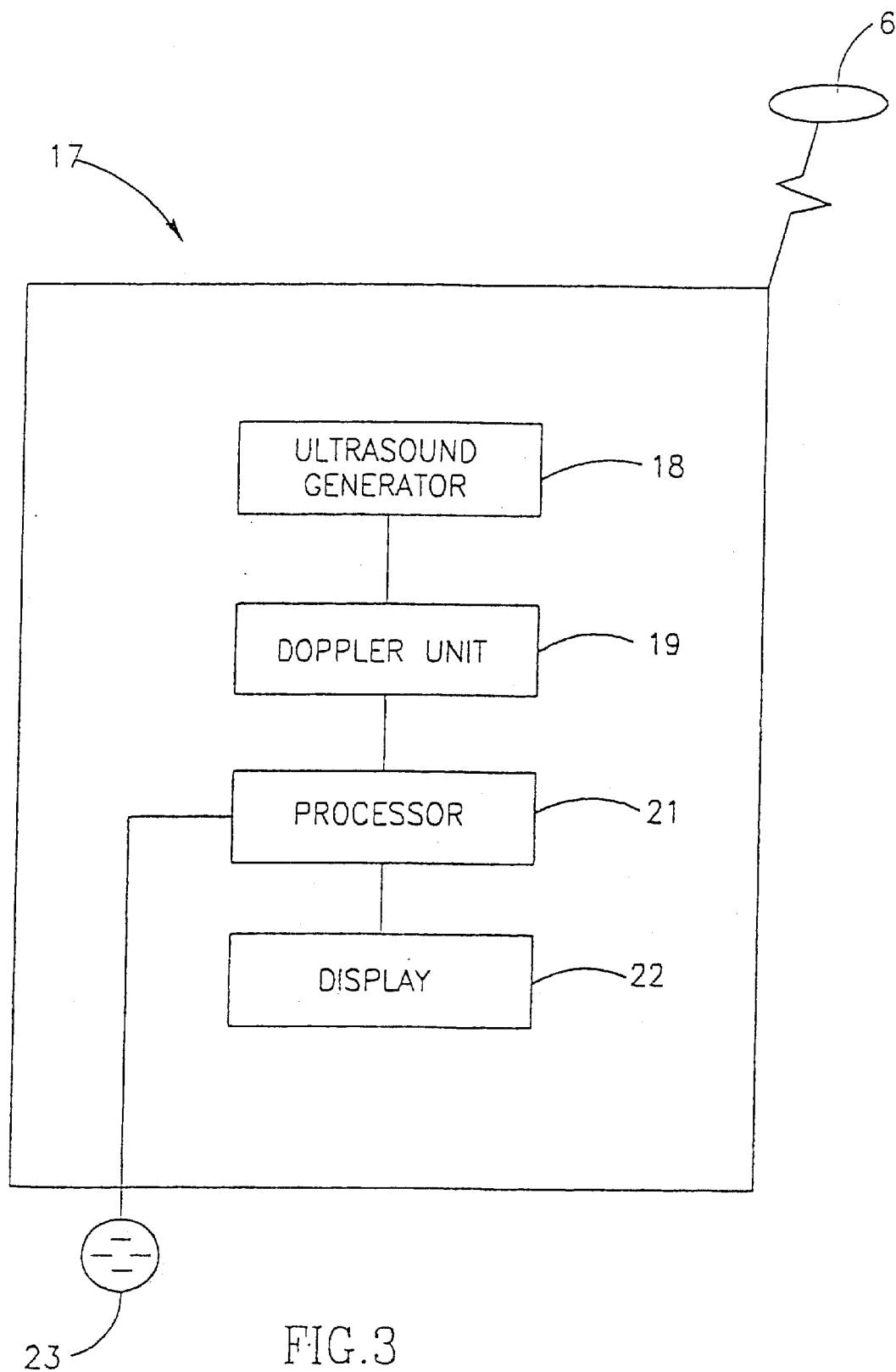
FIG. 3 is a block diagram of a control unit of the system of FIG. 1.

Turning now to FIG. 3, the system 1 also includes a control unit 17 with an ultrasound generator 18 for energizing the ultrasound transducers 7 and 8, a Doppler unit 19 for measuring the Doppler shift frequency at a predetermined number of multi-gated sample volumes $SV_i$ along each of the ultrasound beams 9 and 11, and a processor 21 for determining flow related information for display on a display 22. The display 22 displays the two lengths $L_1$ and $L_2$, a graph of blood flow against time, a graph of blood velocity against time, a graph of blood vessel diameter against time, a graph of representative systolic and diastolic blood flow velocity profiles, average blood flow ABF over a cardiac cycle, an index of blood vessel elasticity BVE over a cardiac cycle, an index of shear rate SR, and a time dependent distal resistance index Rs(t). For the best representation of the blood flow velocity as the function of time, a location of a corresponding gate should be determined. This location is determined as the center of the length (chord) L1 and L2 for each beam, respectively. The method of the present invention allows for automatically defining the best location for determining and displaying the time dependence of the blood flow velocity, immediately after the determination of the chords. The control unit 17 also includes a beeper 23 for issuing audible signals at a predetermined time in the subject's cardiac cycle, for example, at peak systole for facilitating manual set-up of the system 1.

With reference now to FIGS. 4–9, three implementations 6A, 6B and 6C of the dual ultrasound transducer probe 6 are now described, each probe having a pair of ultrasound transducers 7 and 8 which are displaceable in tandem and whose ultrasound transducer 8 is rotatably mounted about the so-called fixed ultrasound beam axis 12.

Figure 4:
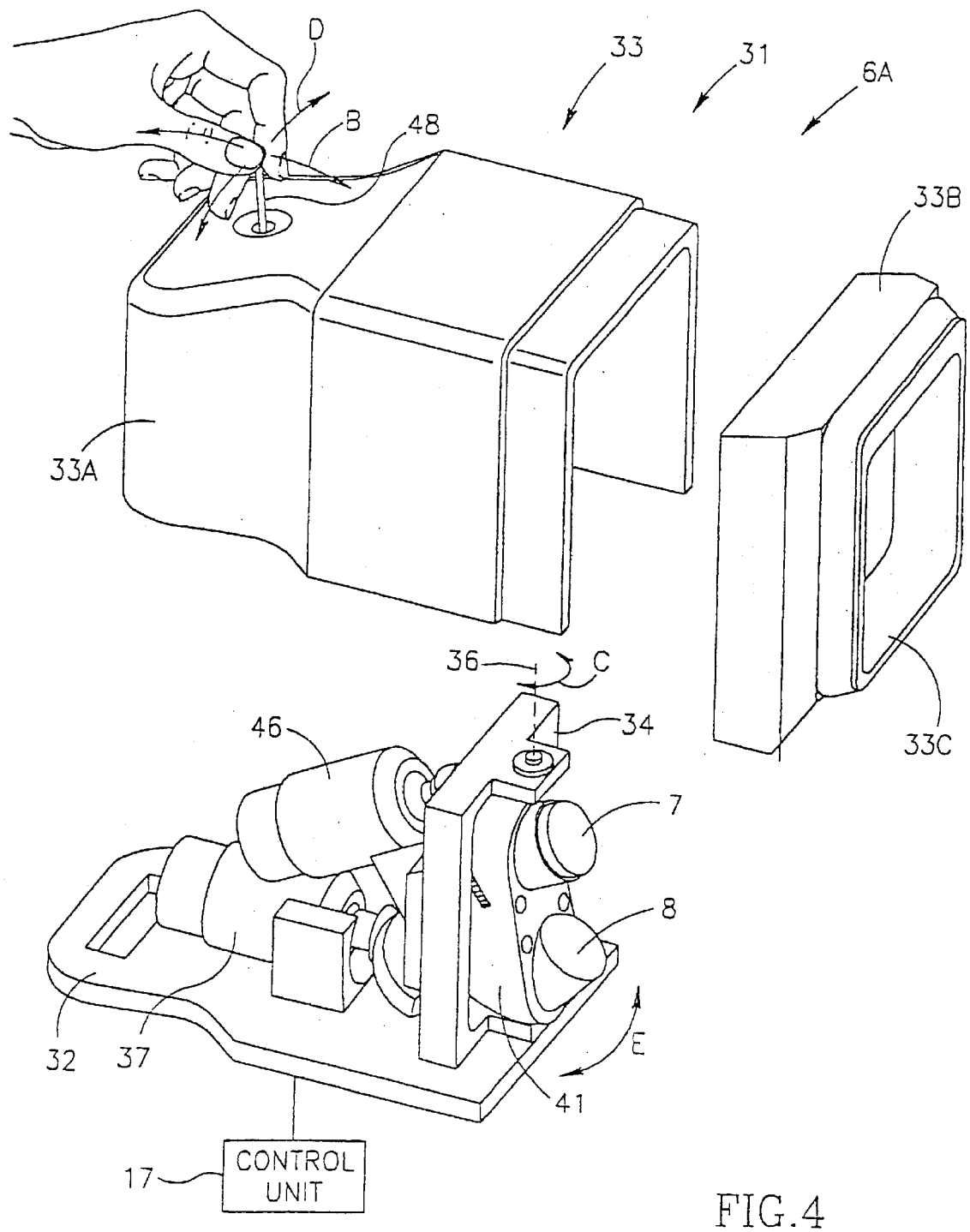
FIG. 4 is a pictorial representation showing a first embodiment of a partially disassembled dual ultrasound transducer probe for use with the system of FIG. 1.
Figure 5:
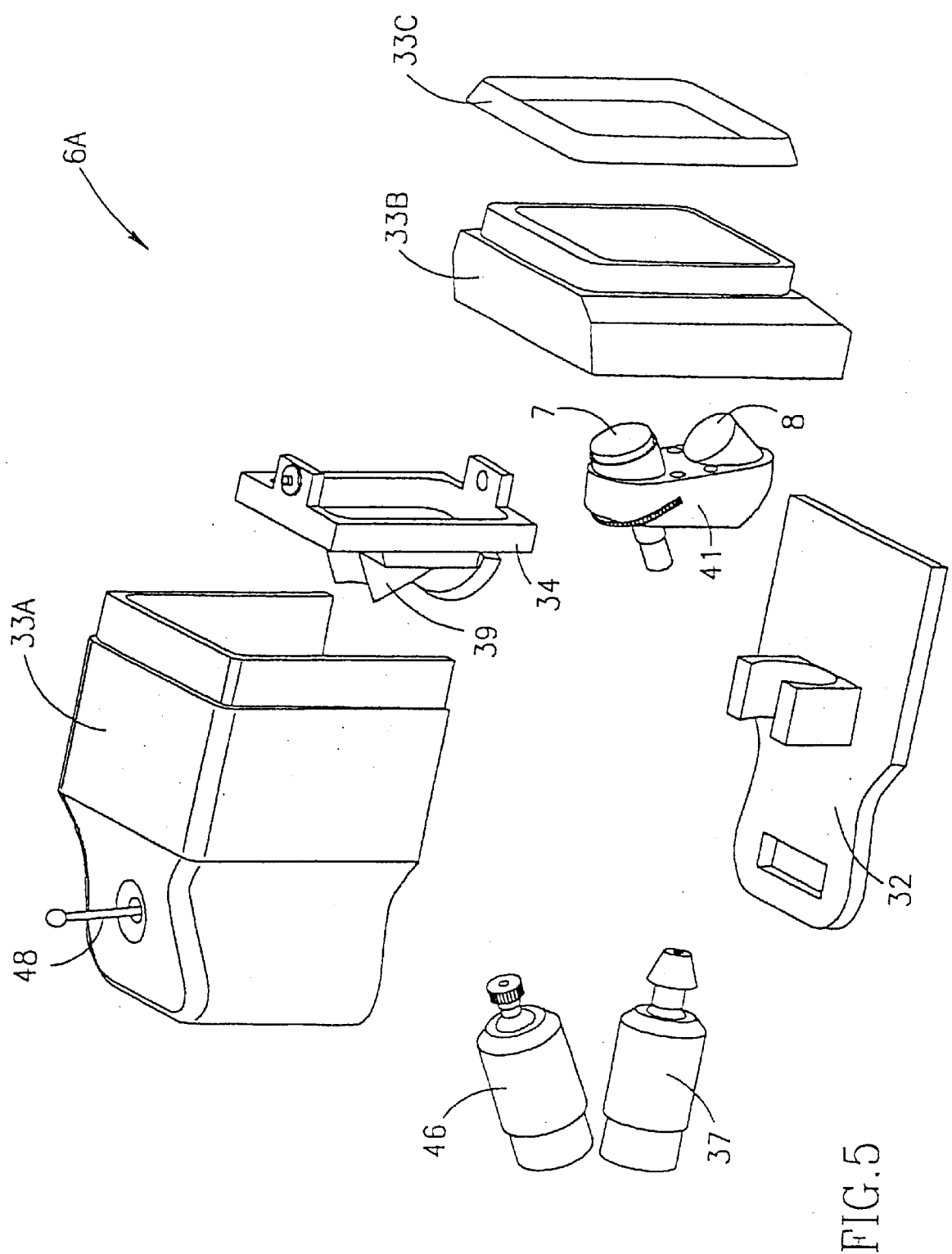
FIG. 5 is an exploded pictorial representation of the probe of FIG. 4.
Figure 6:
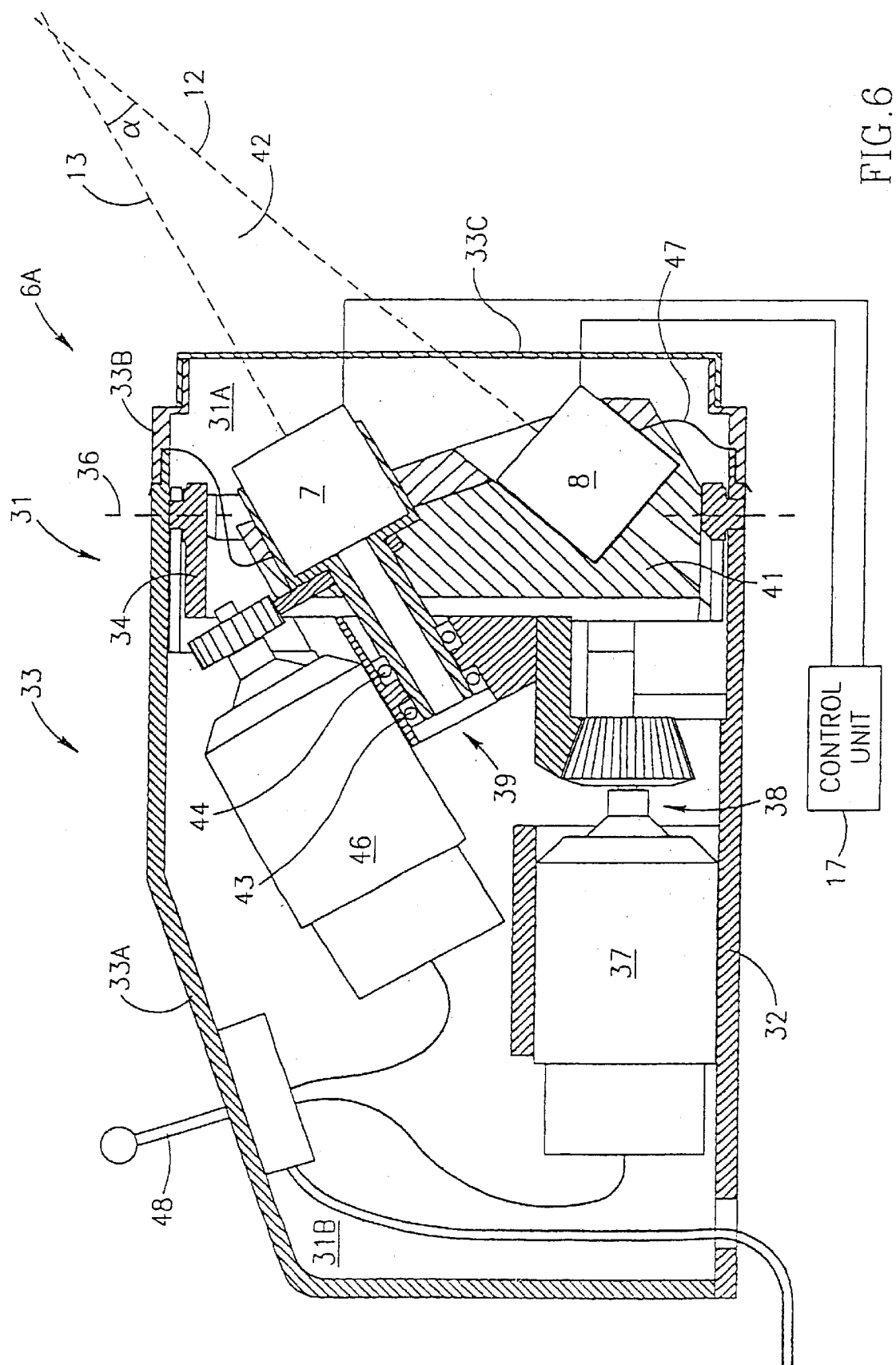
FIG. 6 is a longitudinal cross sectional view of the probe of FIG. 4 along the line VI—VI therein.

With particular reference to FIGS. 4–6, a dual ultrasound transducer probe 6A includes a probe housing 31 with a base plate 32, and a cover 33 consisting of a rear cover portion 33A, a front cover portion 33B, and an ultrasound transmissive window 33C. The base plate 32 rotatably supports a rectangular shaped frame 34 (constituting a support base) about a longitudinal axis 36 by a motor 37 via a straight tooth bevel gear arrangement 38. The frame 34 has a rearward directed bracket 39 for rotatably supporting a support member 41 about an axis of rotation 42 by means of a pair of bearings 43 and 44. The support member 41 carries the ultrasound transducers 7 and 8 having forwardly intercepting ultrasound beam axes 12 and 13, and is driven about the axis of rotation 42 which coincides with the ultrasound beam axis 12 by a motor 46 also supported on the bracket 39. A flexible diaphragm 47 sealing divides the interior of the probe housing 31 into two portions, a front portion 31A accommodating the ultrasound transducers 7 and 8 and filled with a suitable ultrasound transmissive substance, and a rear portion 31B accommodating the motors 37 and 46 (see FIG. 6). A hand operated joystick 48 is provided on the probe housing 31, and is capable of a FORWARD/BACKWARD movement denoted B for correspondingly driving the motor 37 in clockwise/counterclockwise directions for correspondingly rotating the frame 34 in clockwise/counterclockwise directions denoted C, and a LEFT/RIGHT movement denoted D for correspondingly driving the motor 46 in clockwise/counterclockwise directions for correspondingly rotating the support member 41 in clockwise/counterclockwise directions denoted E.

Figure 7:
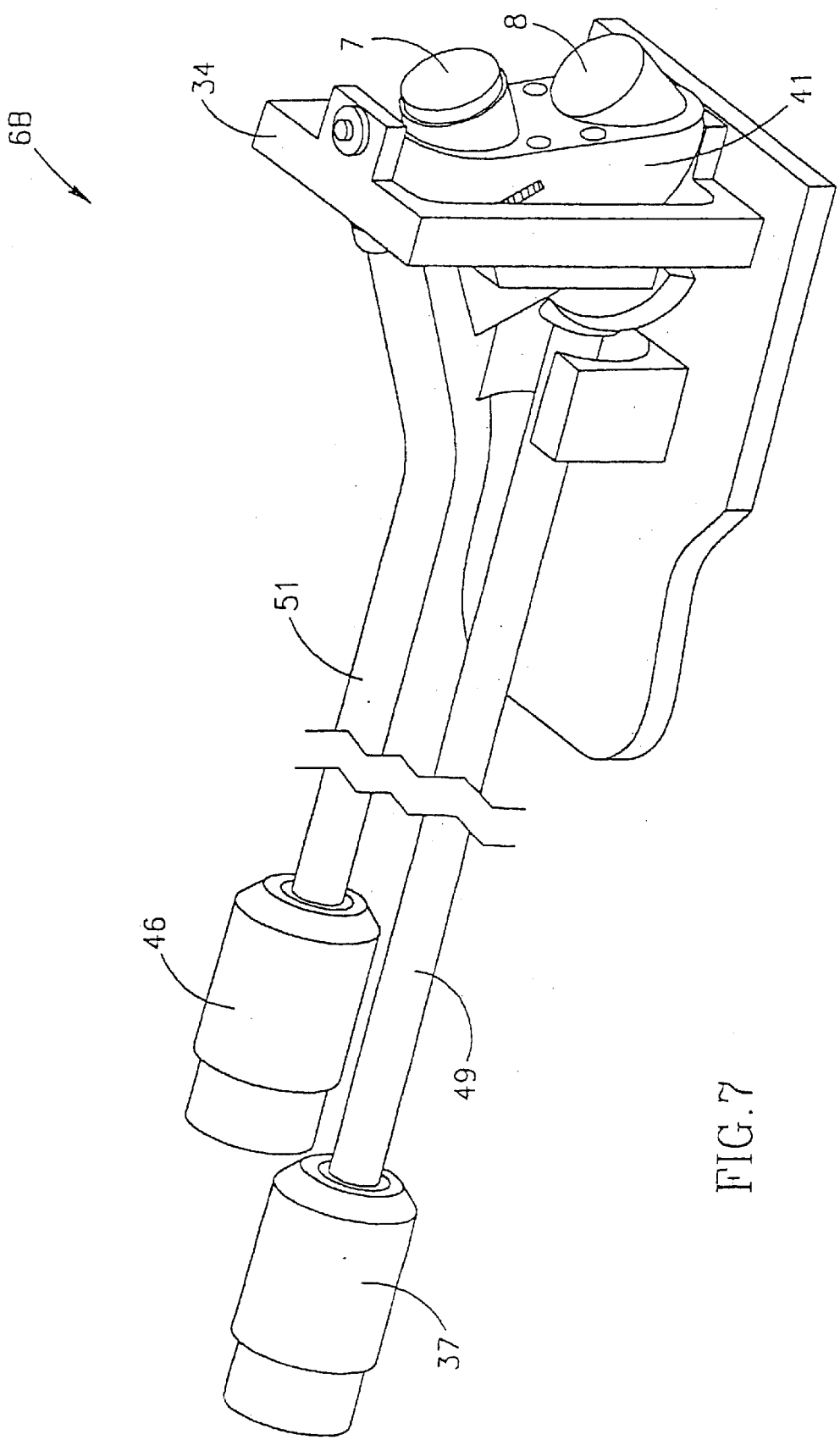
FIG. 7 is a pictorial representation showing a second embodiment of a dual ultrasound transducer probe for use with the system of FIG. 1.

With reference now to FIG. 7, a dual ultrasound transducer probe 6B is similar to the dual ultrasound transducer probe 6A, and identical parts are similarly numbered. The difference between the two probes 6A and 6B is that in the latter, the rotation of the frame 34 and the support member 41 is effected by flexible power transmission cables 49 and 51, respectively, driven by the motors 37 and 46, respectively, which are external to the probe housing 31 whereby its size can be considerably reduced, and flexible diaphragm 47 can be dispensed with.

Figure 8:
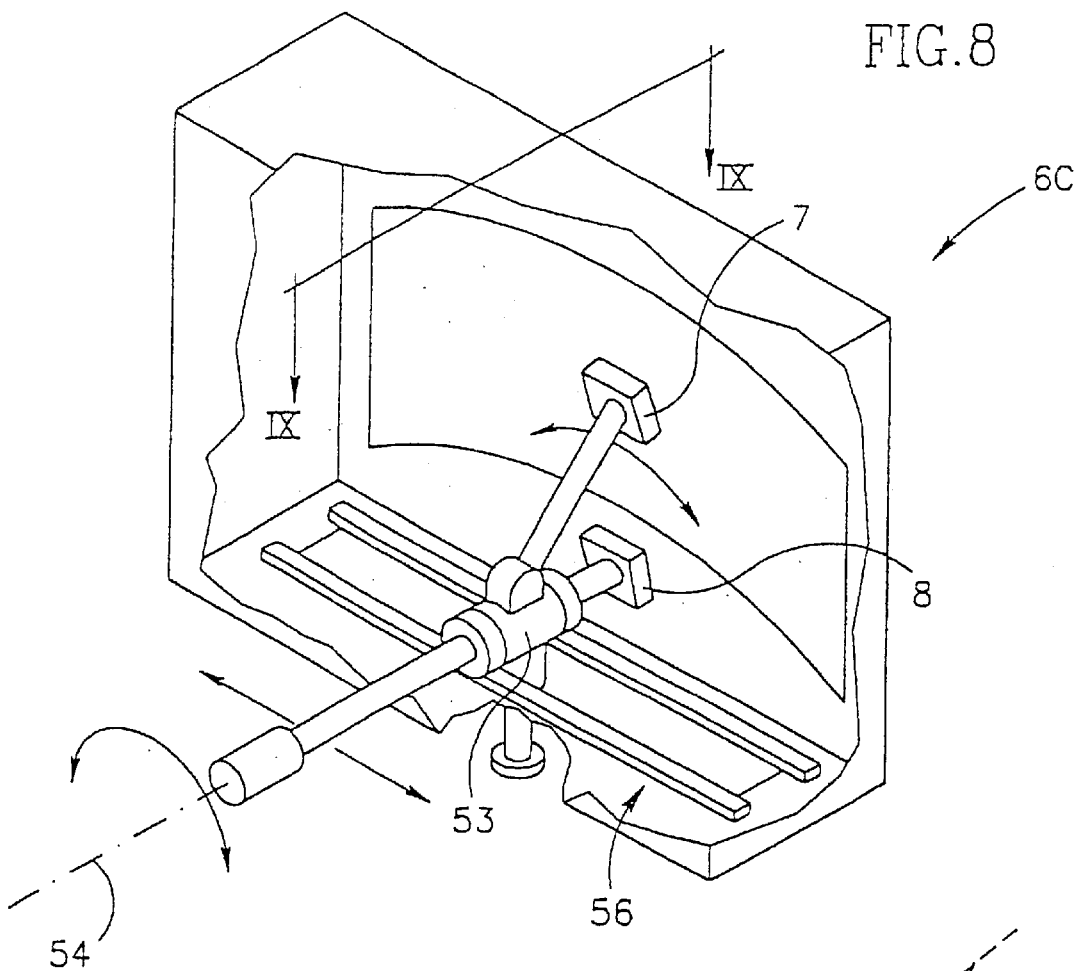
FIG. 8 is a pictorial representation showing a third embodiment of a dual ultrasound transducer probe for use with the system of FIG. 1.
Figure 9:
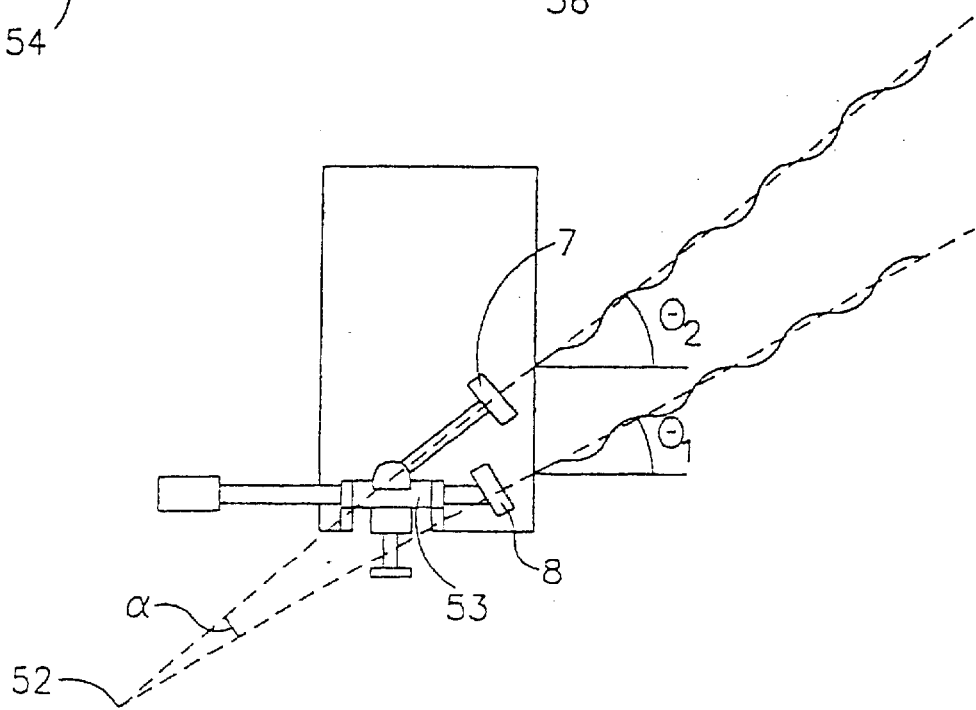
FIG. 9 is a transverse cross sectional view of the probe of FIG. 8 along the line IX—IX therein.

With reference now to FIGS. 8 and 9, a dual ultrasound transducer probe 6C has ultrasound transducers 7 and 8 whose respective ultrasound beam axes 12 and 13 rearwardly intercept at an imaginary interception point 52 at an interception angle $\alpha$ such that $\theta_2=\theta_1+\alpha$. In this case, the ultrasound transducers 7 and 8 are mounted on a support member 53 which can be manually rotated about an axis of rotation 54 which coincides with the ultrasound beam axis 12, and which can be manually slided along a track 56.

Figure 10:
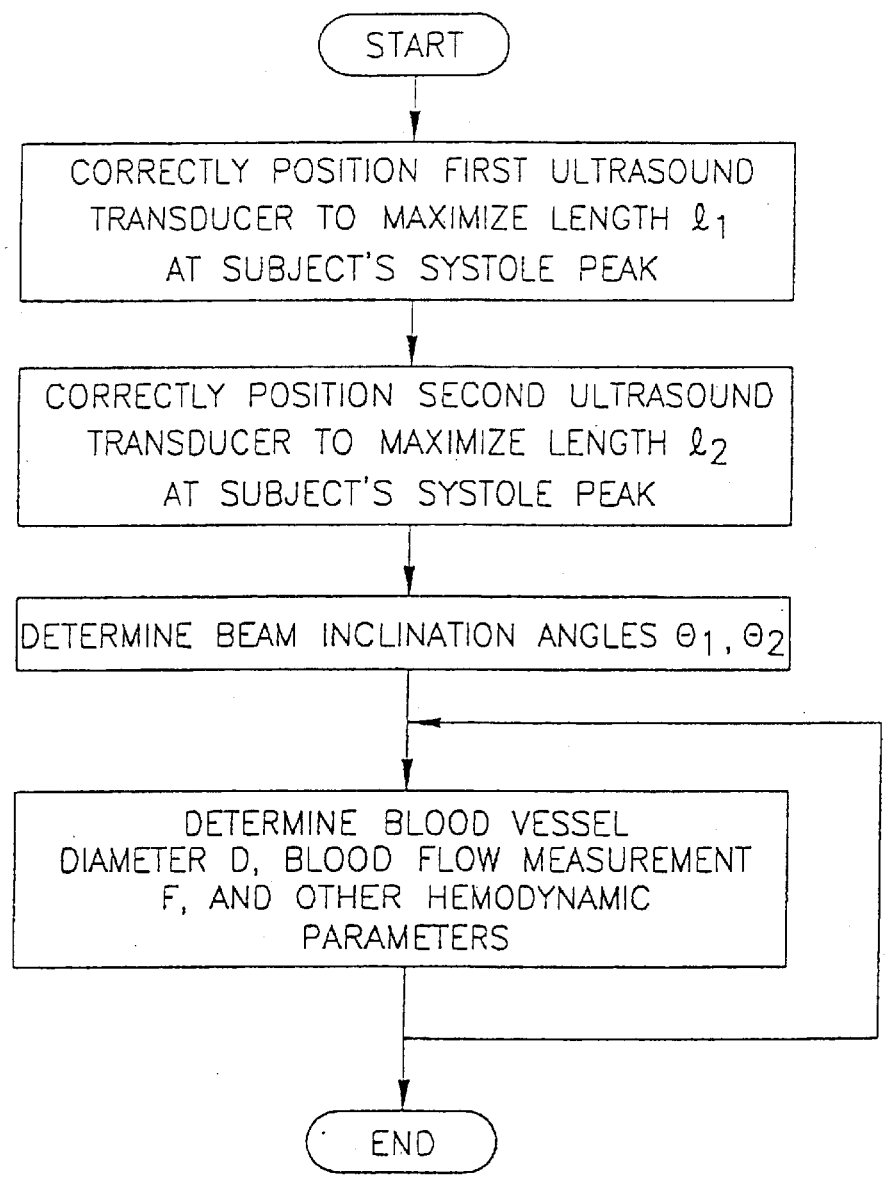
FIG. 10 is a flow diagram illustrating the use and operation of the system of FIG. 1, and a schematic representation showing a blood vessel's cross section for illustrating one approach for blood flow measurement.
Figure 10:
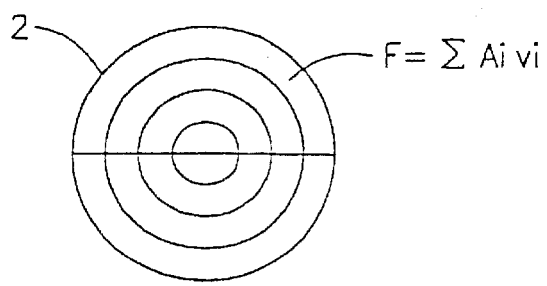

The operation of the system 1 is now described with reference to FIG. 10 for the case that the multi-gated PW ultrasound beams 9 and 11 have 220 gates therealong each, and the system 1 is manually set-up. The probe 6 is attached to a subject's neck adjacent to his carotid artery such that both the ultrasound beams 9 and 11 transverse his carotid artery at substantially but typically not diametrically opposite portions of its wall 3. The ultrasound generator 18 energizes the ultrasound transducers 7 and 8 to transmit the pair of narrow PW ultrasound beams 9 and 11. The Doppler unit 19 measures the Doppler frequency shift within each of a continuous series of small sample volumes $SV_i$ along each of the ultrasound beams 9 and 11. The processor 21 detects the subject's systolic peak after a number of cardiac cycles and proceeds to activate the beeper 23. The processor 21 determines the initial beam corrected chord lengths $L_1$ and $L_2$ of the beam portions 14 and 16 as described hereinbelow with respect to the ultrasound beam 9 only for the sake of convenience, and displays their values on the display 22. The user notes the initial values of the lengths $L_1$ and $L_2$ and manipulates both the ultrasound transducers 7 and 8 in tandem in search of the maximum length $L_1$ indicating that the ultrasound transducer 7 is correctly disposed relative to the subject's carotid artery. On detection of the maximum length $L_1$, the user proceeds to rotate the ultrasound transducer 8 in search of the maximum length $L_2$ whilst maintaining the ultrasound transducer 7 in the same position.

Figure 11:
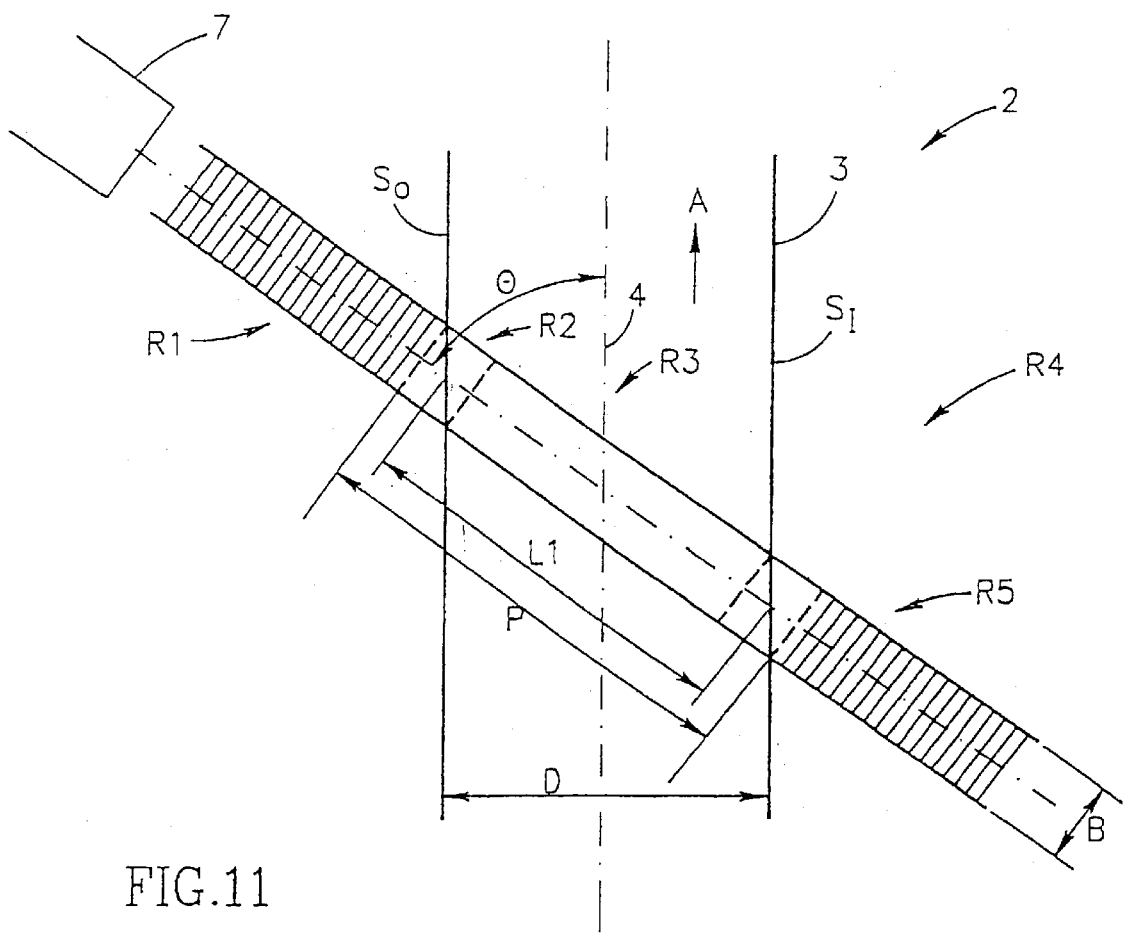
FIG. 11 is a pictorial representation showing a multi-gated Pulse Wave ultrasound beam intercepting a blood vessel.

Reference is made to FIG. 11, showing that the 220 gates along each of the ultrasound beams (the ultrasound beam 9 being shown in the present example) can be divided into five distinct regions as follows: a first region $R_1$ closest to the ultrasound transducer 7 consisting of consecutive gates (1,85) which are wholly exterior to the subject's blood vessel, a second region $R_2$ consisting of consecutive gates (86,90) which partially intercept the outermost surface $S_O$ of the blood vessel's sidewall 3 closest to the ultrasound transducer 7, a third region $R_3$ consisting of consecutive gates (91,155) wholly within the subject's blood vessel, a fourth region $R_4$ consisting of consecutive gates (156,160) which partially intercept the innermost surface $S_I$ of the blood vessel's sidewall 3 furthermost from the ultrasound transducer 7, and a fifth region $R_5$ furthermost from the ultrasound transducer 7 consisting of consecutive gates (161,220) which are wholly exterior to the subject's blood vessel. The measured chord length denoted P of the three intermediate regions $R_2$, $R_3$ and $R_4$ enables determination of the beam corrected chord length L according to the relationship: $L=P-B/\tan\theta$ where B is the beam width of the ultrasound beam, and θ is the acute beam inclination angle subtended between the ultrasound beam axis 9 and the blood vessel's longitudinal axis 4.

Determination of the beam corrected chord length L is in principle a two step process, consisting of the calculation of a 220-component real vector of time averaged amplitude values $E_i$ from a 220×128 matrix of complex reflections amplitude values $E_{ij}$ acquired over 128 excitations of the ultrasound transducer 7, and the detection of the first and last gates along the ultrasound beam 9 which intercept with the outermost surface $S_O$ and the innermost surface $S_I$ of the blood vessel's wall 3 and which are respectively adjacent the ultrasound transducer 7 and remote therefrom. The calculation of the 220-component real vector involves the high pass filtering of the columns of the 220×128 matrix of complex reflections amplitude values $E_{ij}$ along the time coordinate for removing spurious low frequency noise, and thereafter performing either frequency domain operations or time domain operations. The high pass filtering procedure is associated with the fact that the high frequency signals are associated with moving objects, namely, blood within the blood vessel, and therefore enables to define the blood vessel walls.

Figure 12:
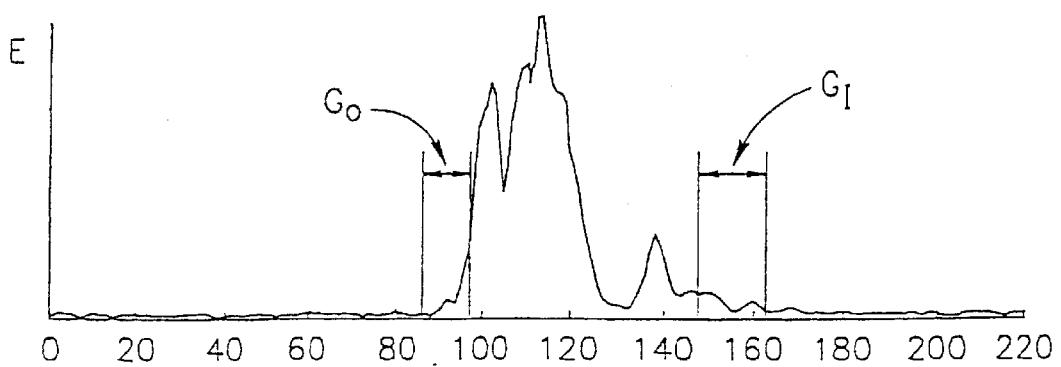
FIG. 12 is a pictorial representation graphically showing a vector of energy values $E_i$ along a multi-gated Pulse Wave ultrasound beam intercepting a blood vessel.
Figure 13:
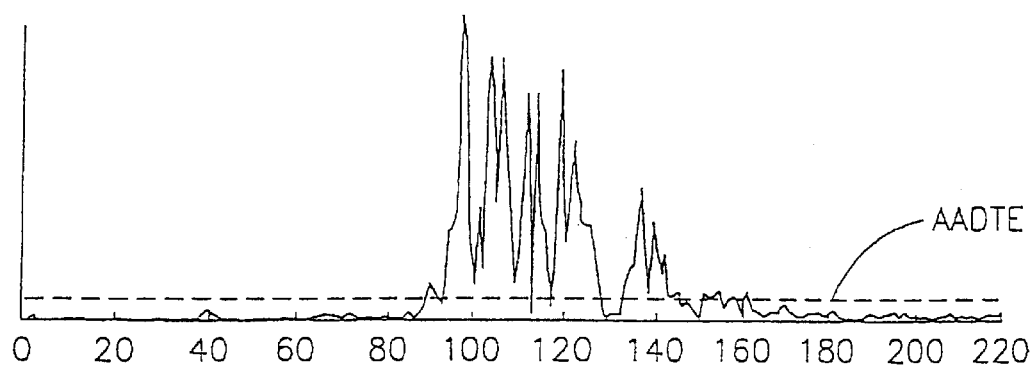
FIG. 13 is a pictorial representation graphically showing the gates along an ultrasound beam whose derivative energy values exceed the value of an AADTE parameter of a thresholding technique for determining the beam corrected chord length L of the portion of an ultrasound beam intercepting a blood vessel.

The frequency domain operations include executing a complex Fast Fourier Transform (FFT) on the 220×128 two dimension matrix of reflections amplitudes $E_{ij}$, summing the spectral intensities $I_{ij}$ for each column j=1 to 128 of the 220×128 complex matrix $I_{ij}$ resulting from the FFT according to the relationship:

$$\sum_{j=1}^{m} \sqrt{(Iij_{\text{Real}})^2 + (Iij_{\text{Image}})^2}$$

and repeating the summation operation for each gate i=1 to 220 along the ultrasound beam 9 so as to obtain a vector of 220 energy values $E_i$ shown graphically in FIG. 12.

Figure 14:
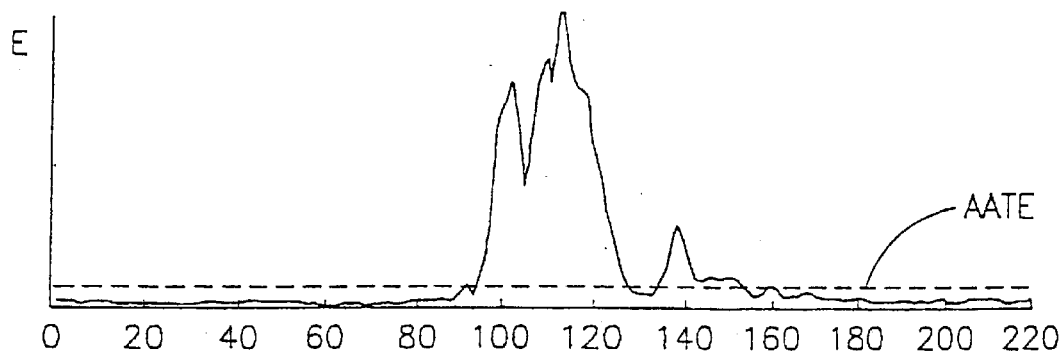
FIG. 14 is a pictorial representation graphically showing the gates along an ultrasound beam whose energy values $E_i$ exceed the value of an AATE parameter of a thresholding technique for determining the beam corrected chord length L of the portion of an ultrasound beam intercepting a blood vessel.

The time domain operations include summing the real amplitudes values $E_{ij}$ for each column j=1 to 128 of the 220×128 matrix of complex reflections amplitude values $E_{ij}$ according to the above relationship:

$$\sum_{j=1}^{m} \sqrt{(Eij_{\text{Real}})^2 + (Eij_{\text{Image}})^2}$$

and repeating the summation operation for each gate i=1 to 220 along the ultrasound beam 9 so as to obtain the 220-component vector of time averaged reflection amplitude values $E_i$ also shown in graphically in FIG. 14. Alternatively, either the real part only or the imaginary part only of the matrix $E_{ij}$ for each column j=1 to 128 of the 220×128 two-dimension matrix $E_{ij}$ can be summed.

On the basis of the vector of 220 values $E_i$, two approaches can be employed for determining the measured chord length P as follows: parametric estimation involving the detection of the first and last parabolic like portions along the vector $E_i$, or alternatively thresholding techniques. Parametric estimation is by way of examination of consecutive groups of 20 consecutive gates along the ultrasound beam 9, thereby specifying 200 consecutive groups therealong, and includes the following steps: calculating the coefficients a, b and c of the equation: $y=a+bE_i+cE_i^2$ for 200 groups of consecutive gates (i, i+20) for i=1 to 200; calculating an innermost boundary (leftmost in the Figures) identification value $T_{left}$ according to the relationship:

$$T = \frac{c}{\sqrt{(a^2 + b^2)}}$$

for each group of 20 consecutive gates; and determining the group of consecutive gates closest to the ultrasound transducer 7 denoted $G_O$ which has the maximum $T_{left}$ value of the 200 $T_{left}$ values (see FIG. 12). Of this group of consecutive gates $G_O$, the outermost surface $S_O$ of the blood vessel's sidewall 3 is assumed to be the group's first gate closest to the ultrasound transducer 7 which in this case is gate 85 bordering between the regions $R_1$ and $R_2$. These steps are then repeated for the gates along the ultrasound beam 9 in the reverse direction for determining the group of consecutive gates with the maximum outermost boundary (rightmost in the Figures) identification value $T_{right}$ value of the again 200 $T_{right}$ values denoted $G_I$ (see FIG. 12). Of this group of consecutive gates $G_I$, the innermost surface $S_I$ of the blood vessel's sidewall 3 is assumed to be the group's last gate furthermost from the ultrasound transducer 7 which in this case is gate 165 bordering between the regions $R_4$ and $R_5$.

One thresholding algorithm involves selecting all gates along the ultrasound beam 9 (and along the other beam as well) which satisfy the conditions $E_i \geq$ AADTE and $E_i \geq$ AATE where the value of so-called average absolute derivative threshold energy AADTE of the vector of 220 values $E_i$ is calculated according to the relationship:

$$AADTE = \frac{1}{n}\sum_{i=1}^{n} |E_{i+1} - E_i|$$

and the value of the so-called average amplitude threshold energy AATE of the vector of 220 values $E_i$ is calculated according to the relationship:

$$AATE = \frac{\text{mean of } E_i \text{ values} + \text{median of } E_i \text{ values}}{2}$$

Figure 15:
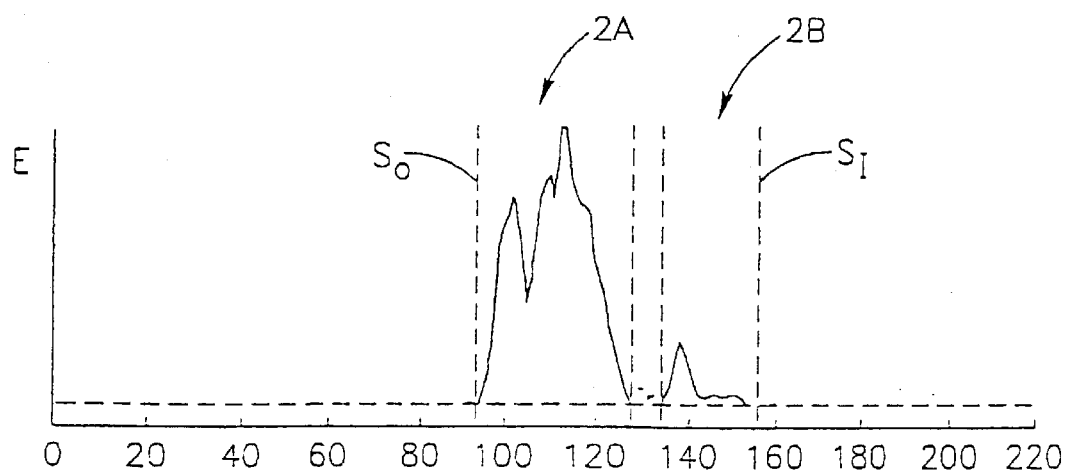
FIG. 15 is a pictorial representation showing the graph of FIG. 14 with the gates whose energy values $E_i$ satisfy the conditions $E_i \geq$ AADTE and $E_i \geq$ AATE.

This approach may render so-called multiple humped graphs ostensibly indicating the presence of several phantom blood vessels as represented by the pair of phantom blood vessels 2A and 2B which must be necessarily combined to render the single blood vessel 2 (see FIG. 15). This can be achieved by the following algorithm: generating a g single dimension vector K of all the gates i=1 to 220 along the ultrasound beam whose energy value $E_i$ satisfies the conditions $E_i \geq$ AADTE and $E_i \geq$ AATE; generating a h single dimension vector DK where $DK_h = K_{h+1} - K_h$ for h=1 to g; calculating the parameter Average DK according to the relationship:

$$\text{Average} DK = \frac{1}{g}\sum_{h=1}^{g} DK_h$$

determining the innermost region of gates which satisfies the condition $DK_h/2 \geq$ Average DK and specifying that the innermost gate of the innermost region is the outermost surface $S_O$; and determining the outermost region of gates which satisfies the condition $DK_h/2 \geq$ Average DK, and specifying that the rightmost gate of the rightmost region is the innermost surface $S_I$. For example, for a vector $DK_h =$ [1,1,1,1,1,1,3,1,1,4,1,1,1,1], Avg DK=19/14, the so-called innermost region is where DK=3, the so-called outermost region is where DK=4, the innermost gate of the innermost region DK=3 is the outermost surface $S_O$, and the outermost gate of the outermost region DK=4 is the innermost surface $S_I$.

Figure 16A:
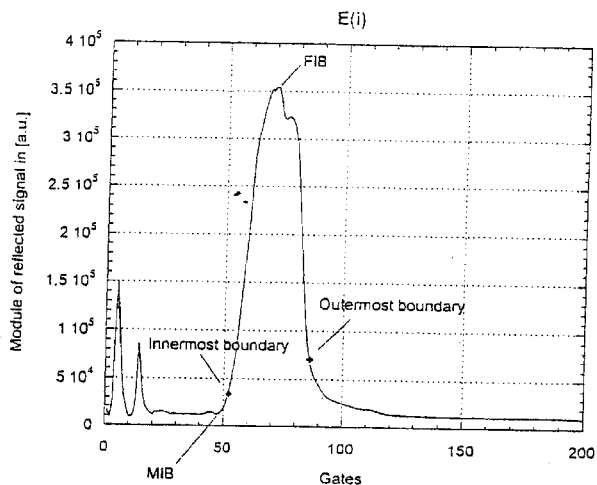
FIGS. 16A to 16C illustrate the principles of an alternative technique suitable for the vessel walls' detection, representing respectively, a time averaged and filtered module of the reflections amplitude E(i) as a function of the gate coordinate along the ultrasound beam, the first derivative DE(i) of the function E(i), and the second derivative of the function E(i)
Figure 16B:
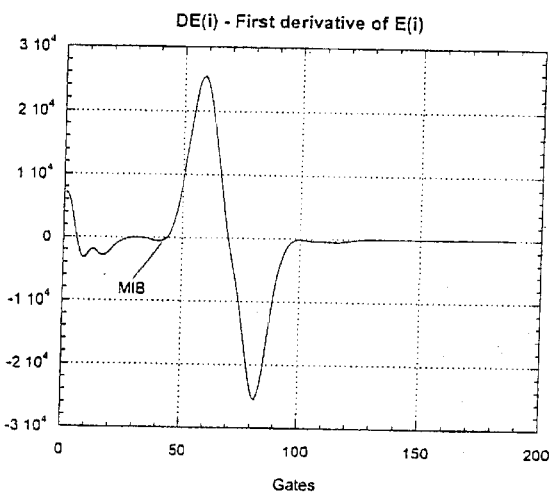
Figure 16C:
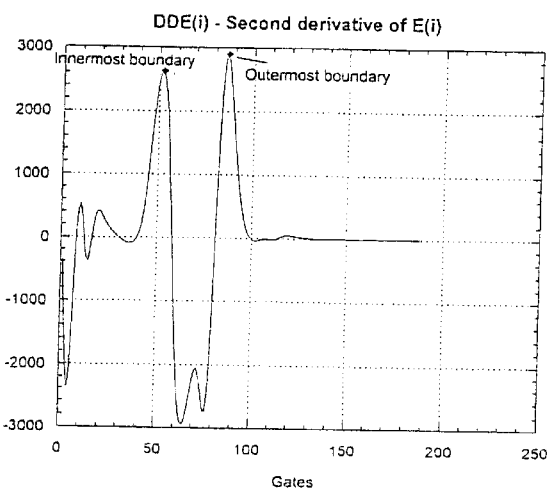

FIGS. 16A–16C illustrate the principles of another algorithm for boundary detection relating to threshold technique, which involves analysis of the first and second derivatives $DE_i$ and $DDE_i$ (FIGS. 16B and 16C) of a function E(i) (shown in FIG. 16A) along the ultrasound beam. The dependence of the module of reflection signal on the gate coordinate, which is represented by the vector $E_i$, can be considered as a function of the reflection amplitude values E(i) along the beam (gates), i.e., E(i). The behavior of this function is irregular due to interference effects. To smooth the function E(i), the low passed filter is implemented. The smoothness of signal can be also improved by additional averaging of E(i) on time, that means that several vectors $E_i$ measured at successive moments of time are summed. The number of averaging defines the time interval during which the values $E_i$ and then of the chord L and diameter D, are calculated. This time interval can include one or several cardiocycles, or some particular time interval inside the cardiocycle, preferably systole or diastole. The corresponding chord value or vessel diameter for these cases will represent the averaged values for one cardiocycle or specifically systolic and diastolic values. In the example of FIG. 16A, the function E(i) is averaged on one cardiocycle, and then filtered.

To find the blood vessel boundaries, the algorithm first narrows the searching area. To this end, the initial and ending 10 gates are disregarded from consideration, because the values of function E(i) in these regions are changed by transient filter characteristics. For the innermost boundary, the algorithm defines the far limit of the searching area FIB as the gate number correspondent to the global maximum of the function E(i).

Then, the algorithm searches the last minimum of the function E(i), which is designated MIB in FIGS. 16A and 16B and which satisfies the following condition: DE(i−1) ≦0, DE(i)>0, where i=10, . . . , FIB. The innermost vessel boundary position is determined as the maximum of the second derivative DDE(i) within the interval i=MIB, . . . , FIB. As for the outermost boundary, the searching area is started from the global minimum of the second derivative DE(i), where i>FIB, and is ended at the gate number 210. The outermost boundary position is determined as the maximum of the second derivative DDE(i) of the function E(i), where FIB<i<210.

After correct positioning, the processor 21 determines the beam inclination angles $\theta_1$ and $\theta_2$ using the conventional Doppler equation on the assumption that an identical peak or average blood velocity is measured along both of the two ultrasound beams 9 and 11. Thereafter, based on the assumption that the blood vessel in the region of insonation has a circular cross section which changes in a radial fashion, the processor 21 continuously calculates the blood vessel's diameter D for each of the two ultrasound beams 9 and 11 according to the relationship: D=L sin θ, and averages the results for display on the display 22. By this, the center of the blood vessel can be determined, and therefore the profile of the velocity in this central region. Based on this measurement, the processor 21 calculates blood flow measurement according to the product of A and $v_{avg}$ where A is the blood vessel's cross section area and $v_{avg}$ is the average blood flow speed. Alternatively, blood flow measurement can be calculated according to $\Sigma A_i v_i$ where $A_i$ is the semi-annular cross sectional area associated with a sample volume $SV_i$ and $v_i$ is the measured blood flow speed at a particular sample volume $SV_i$ (see FIG. 10).

Finally, the processor 21 determines other blood flow information for display on the display 22 as follows:

First, a time dependent index of the distal resistance Rs(t) according to the relationship:

$$Rs(t) = \frac{Pr(t)}{F(t)}$$

where Pr(t) is the time dependent arterial blood pressure Pr; and F(t) is the instantaneous blood flow.

Second, index of shear rate at the outermost surface $S_O$ and the innermost surface $S_I$ of the blood vessel's sidewall 3 with respect to the ultrasound probe 6 according to the relationship:

$$\frac{dV}{dD} \text{ at } D = 0, \text{ and } D.$$

And lastly, blood vessel elasticity according to the relationship:

$$\frac{D_s - D_d}{D_d}$$

where $D_s$ is the blood vessel diameter at peak systole and $D_d$ is the blood vessel diameter at diastole.

While the invention has been described with respect to a limited number of embodiments, it will be appreciated that many variations, modifications and other applications of the invention can be made within the scope of the claims appended hereto. For example, the probes 6A and 6B can be implemented with rearwardly intercepting ultrasound beam axes as implemented in probe 6C whilst the probe 6C can be implemented with the forwardly intercepting ultrasound beam axes as implemented in the probes 6A and 6B. Also, the manipulation of the ultrasound transducers into their correct positioning relative to a blood vessel's longitudinal axis can be performed automatically.

What is claimed is:

1. A Doppler based ultrasound measurement apparatus for blood flow measurement, comprising:
   a dual ultrasonic transducer probe comprising a housing containing first and second ultrasound transducers each operable in transmitting and receiving modes, the transducers producing first and second ultrasound beams propagating, respectively, along first and second beam propagation axes, the first and second beam propagation axes, wherein the first and second transducers are oriented with respect to each other such that the first and second beam propagation axes intersect at a certain acute angle, and are displacable with respect to a patient's blood vessel to enable desired positioning of the probe such that each of the first and second beam propagation axes intersects a longitudinal axis of the blood vessel, and
   a control unit connectable to the prove device, the control unit being operable to energize the first and second ultrasound transducers to operate in a pulse wave transmission mode and receive ultrasound signals from multi-gated sample volumes along the first and second propagation axes, respectively, and being operable to process data indicative of the signals received from each of the first and second transducers during a displacement of the transducers with respect to the blood vessel to carry out preliminary measurements of a diameter of the blood vessel to thereby detect the desired positioning of the transducers relative to the blood vessel as that corresponding to equal and maximal values of the diameters calculated for both the first and second beams.

2. The apparatus according to claim 1, wherein the housing has an elongated shape, the first and second transducers being mounted at a distal end of the housing, the manual displacement of the housing with real-time analysis of the preliminary measurements allowing said desired positioning of the transducers.

3. The apparatus according to claim 1, wherein said probe device comprises a support member supporting said first and second ultrasound transducers, the support member being rotatable about said first beam propagation axis whereby said second ultrasound transducer rotates about said first beam propagation axis, and is displacably mounted in said housing for displacing said first and second ultrasound transducers in tandem, the arrangement being such that both said first and second beam propagation axes intercept the blood vessel's longitudinal axis and correspondingly subtend acute beam inclination angles $\theta_1$ and $\theta_2$ therewith for enabling the measurement of Doppler shift frequencies along said first and second beam propagation axes.

4. The apparatus according to claim 3, wherein said support member is rotatably mounted on a support base about said first beam propagation axis, and said support base is rotatably mounted about a longitudinal axis of said housing whereby said first and second ultrasound transducers are rotatable in tandem about said longitudinal axis of the housing.

5. The apparatus according to claim 4 wherein said probe device further comprises a motorized means for rotating said support member about said first beam propagation axis, and said support base about its longitudinal axis.

6. The apparatus according to claim 5, wherein said motorized means includes a pair of motors external to said housing.

7. The apparatus according to claim 3 and further comprising a hand operated joystick for controlling the motion of said support member.

8. The apparatus according to claim 3, wherein said pair of ultrasound transducers are rectilinearly displaced in tandem in said housing.

9. A blood vessel diameter determination method utilizing the dual ultrasonic transducer probe comprising a housing containing first and second ultrasound transducers each operable in transmitting and receiving modes, the transducers producing first and second ultrasound beams propagating, respectively, along first and second beam propagation axes, the first and second beam propagation axes, wherein the first and second transducers are oriented with respect to each other such that the first and second beam propagation axes intersect at a certain acute angle, the method comprising:

(a) providing desired positioning of the transducers, relative to a blood vessel under measurements, in which each of the first and second beam propagation axes intersects the longitudinal axis of the blood vessel, said desired positioning being provided by providing a displacement of the transducers with respect to the blood vessel and performing preliminary measurements of the blood vessel diameter;

(b) carrying out measurements to determine the blood vessel diameter by energizing the first and second ultrasound transducers to insonate the blood vessel with the first and second pulsed wave ultrasound beams, respectively, and receiving an amplitude vector of reflections with Doppler shifted frequencies for each of the ultrasound beams, wherein said amplitude vector of reflections is an n-element vector formed by complex values of the amplitudes from n successive coordinates along the ultrasound beam vector representing n successive gates;

(c) repeating step (b) m times and obtaining an n×m two-dimensional matrix of the reflection amplitudes $E_{ij}$, wherein i is the gate coordinate along the beam axis, i=1, . . . , n, and j is the time coordinate, j=1, . . . , m, each of the reflection amplitude values being complex and being representative of the amplitude and phase of the reflection at the respective gate at a certain time; and (d) processing said matrix to calculate the blood vessel diameter.

10. The method according to claim 9, wherein said preliminary measurements ensuring that the axes of the beams intercept with the longitudinal axis of the blood vessel includes measurements of the vessel diameter associated with the first and second beams, respectively, and the displacement of the probe until equal and maximal values of diameters are measured for both beams.

11. The method according to claim 9, wherein said processing comprises the steps of:

applying a high pass filtering to said matrix of the reflection amplitude values $E_{ij}$ along j-dimension to remove values relating to a low frequency part of reflection signals, thereby removing reflection signals associated with blood vessel walls;

processing a filtered matrix of the reflection amplitude values for each of the beams to calculate an n-element real vector of time averaged amplitudes $E_i$ along the beam propagation axis, and analyzing the calculated real vector for each of the beams to determine a corrected chord length L of a portion of the ultrasound beam extending between an outermost surface $S_O$ and an innermost surface $S_I$ of the blood vessel's wall correspondingly adjacent the ultrasound transducer, and remote therefrom;

utilizing the corrected chord length L and a beam inclination angle for each of the beams to calculate the blood vessel diameter.

12. A blood vessel diameter determination method comprising the steps of:

(e) providing a desired positioning of first and second ultrasound transducers relative to the blood vessel to ensure that each of first and second ultrasound beam propagation axes intercepts the blood vessel's longitudinal axis and subtends, the transducers being oriented with respect to each other such that the first and second beam propagation axes are interceptable at an acute angle, the desired positioning being provided by displacing the transducers with respect to the blood vessel and performing preliminary measurements of the blood vessel diameter;

(f) carrying out measurements to determine the blood vessel diameter by energizing the first and second ultrasound transducers to insonate the blood vessel with first and second pulsed wave ultrasound beams, respectively, and receiving an amplitude vector of reflections with Doppler shifted frequencies for each of the ultrasound beams, wherein said amplitude vector of reflections is an n-element vector formed by complex values of the amplitudes from n successive coordinates along the ultrasound beam vector representing n successive gates;

(g) repeating step (b) m times and obtaining an n×m two-dimensional matrix of the reflection amplitudes $E_{ij}$, wherein i is the gate coordinate along the beam axis, i=1, . . . , n, and j is the time coordinate, j=1, . . . , m, each of the reflection amplitude values being complex and being representative of the amplitude and phase of the reflection at the respective gate at a certain time; and (h) processing said matrix to calculate the blood vessel diameter.

13. The method according to claim 12, wherein said preliminary measurements ensuring that the axes of the beams intercept with the longitudinal axis of the blood vessel includes measurements of the vessel diameter associated with the first and second beams, respectively, and the displacement of the probe until equal and maximal values of diameters are measured for both beams.

14. The method according to claim 12, wherein said processing comprises the steps of:

applying a high pass filtering to said matrix of the reflection amplitude values $E_{ij}$ along j-dimension to remove values relating to a low frequency part of reflection signals, thereby removing reflection signals associated with blood vessel walls;

processing a filtered matrix of the reflection amplitude values for each of the beams to calculate an n-element real vector of time averaged amplitudes $E_i$ along the beam propagation axis, and analyzing the calculated real vector for each of the beams to determine a beam corrected chord length L of a portion of the ultrasound beam extending between an outermost surface $S_O$ and an innermost surface $S_I$ of the blood vessel's wall correspondingly adjacent the ultrasound transducer, and remote therefrom; and utilizing the corrected chord length L and a beam inclination angle for each of the beams to calculate the blood vessel diameter D.

15. The method according to claim 14, wherein the calculation of the n-element real vector $E_i$ of the time averaged amplitudes along each of the ultrasound beams includes the steps of:

(1) performing a complex Fast Fourier Transform operation on the n×m two-dimensional matrix of the reflection amplitude values $E_{ij}$, thereby obtaining an n×m complex matrix of spectral amplitudes $I_{ij}$, wherein i is the gate coordinate and j is an integer frequency index;

(2) summing the values $I_{ij}$ along the frequency index for each column j =1 to m of the matrix $I_{ij}$ according to the relationship:

$$\sum_{j=1}^{m} \sqrt{I_{ij\,Real}^2 + I_{ij\,Image}^2} \; ; \text{and.}$$

16. The method according to claim 14 wherein the calculation of the n-element real vector of the time averaged amplitudes $E_i$ along each of the ultrasound beams includes the steps of:

(1) summing the values $E_{ij}$ for each column j=1 to m of the n×m two-dimension matrix of the reflection amplitude values $E_{ij}$ according to the relationship:

$$\sum_{j=1}^{m} \sqrt{E_{ij\,Real}^2 + E_{ij\,Image}^2} \; ; \text{and}$$

(2) repeating step (1) for each gate i=1 to n along the ultrasound beam.

17. The method according to claim 14, wherein the calculation of the n-element real vector $E_i$ of the time averaged amplitudes along each of the ultrasound beams includes the steps of:

(1) summing the real part or the imaginary part of the values $E_{ij}$ for each column j=1 to m of the n×m two-dimension matrix of the reflection amplitude values $E_{ij}$; and (2) repeating step (1) for each gate i=1 to n along the ultrasound beam.

18. The method according to claim 14, wherein the step of analyzing the calculated real vector for each of the beams to determine the beam corrected chord length L includes the steps of (1) determining a group size s of a group of consecutive gates (i,i+s) along the ultrasound beam, thereby specifying (n–s) groups of consecutive gates therealong;

(2) calculating the coefficients a, b and c of the equation $y=a+bE_i+cE_i^2$ for (n–s) groups of consecutive gates (i,i+s) for i=1 to (n–s);

(3) calculating an innermost boundary identification value $T_{left}$ according to the relationship:

$$T = \frac{c}{\sqrt{(a^2 + b^2)}}$$

for each group of consecutive gates (i,i+s);

(4) determining the first group of consecutive gates along the ultrasound beam adjacent the ultrasound transducer with the maximum $T_{left}$ value of the (n–s) $T_{left}$ values;

(5) selecting the first gate of the first group of consecutive gates closest to the ultrasound transducer as the gate which intercepts with the outermost surface $S_O$ of the blood vessel's sidewall;

(6) repeating steps (2) and (3) for (n–s) groups of consecutive gates for gates (i,i–s) for i=n to s for calculating an outermost boundary identification value $T_{right}$;

(7) determining the last group of consecutive gates along the ultrasound beam remote from the ultrasound transducer with the maximum $T_{right}$ value of the (n–s) $T_{right}$ values;

(8) determining the last gate of the last group of consecutive gates furthermost from the ultrasound transducer as the gate which intercepts with the innermost surface $S_I$ of the blood vessel's sidewall;

(9) determining a beam chord length P from the first gate and the last gate; and

(10) determining the beam corrected chord length L according to the relationship: L=P–B/tan θ where B is the width of the ultrasound beam.

19. The method according to claim 14, wherein the step of analyzing the calculated real vector for each of the beams to determine the beam corrected chord length L includes the steps of:

(1) determining the average absolute derivative threshold energy AADTE of the n-component $E_i$ according to the relationship:

$$AADTE = \frac{1}{n}\sum_{i=1}^{n} |E_{i+1} - E_i|$$

(2) determining the average amplitude threshold energy AATE of the n-component vector $E_i$ according to the relationship:

$$AATE = \frac{\text{mean of } E_1 \text{ values} + \text{median of } E_1 \text{ values}}{2};$$

(3) determining that the first gate along the ultrasound beam closest to the ultrasound transducer whose reflection amplitude values $E_i$ satisfies the conditions $E_i \geq$ AADTE and $E_i \geq$ AATE;

(4) determining the last gate along the ultrasound beam furthermost from the ultrasound transducer whose reflection amplitude values $E_i$ satisfies the conditions $E_i \geq$ AADTE and $E_i \geq$ AATE;

(5) determining a beam chord length P from the first gate and the last gate; and (6) determining the beam corrected chord length L according to the relationship: L=P−B/tan θ where B is the width of the ultrasound beam.

20. The method according to claim 19 wherein the step (6) includes the steps of:

(7-1) generating a g one-dimensional vector K of all the gates i=1 to n along the ultrasound beam whose reflection amplitude value $E_i$ satisfies the conditions $E_I \geq$ AADTE and $E_i \geq$ AATE;

(7-2) generating a h one-dimensional vector DK where $DK_h = K_{h+1} - K_h$ for h=1 to g;

(7-3) calculating the parameter Average DK according to the relationship:

$$AverageDK = \frac{1}{g}\sum_{h=1}^{g} DK_h$$

(7-4) determining the innermost region of gates which satisfies the condition $DK_h/2 \geq$ Average DK, and specifying that the innermost gate of the innermost region is the outermost surface $S_O$; and (7-5) determining the outermost region of gates which satisfies the condition $DK_h/2 \geq$ Average DK and specifying that the outermost gate of the outermost region is the innermost surface $S_I$.

21. The method according to claim 14, wherein the analyzing of the calculated real vector for each of the beams to determine the beam corrected chord length L includes the steps of:

(1) time averaging and filtering of the vector $E_i$ by a low pass filtering to exclude reflection amplitude oscillation along the ultrasound beam due to an interference effect, thereby obtaining a smooth function E(i) of module of reflection amplitude upon the coordinate along the ultrasound beam;

(2) calculating a first derivative DE(i) and a second derivative DDE(i) of the function E(i) along the gate coordinate; and (3) analyzing the first and second derivatives to determine the innermost and ourtermost boundaries of the blood vessel.

22. The method according to claim 21, wherein said analyzing and determination of the boundaries comprises the steps of:

defining an end gate coordinate for searching the innermost boundary FIB as of a global maximum of the function E(i);

determining a coordinate of a last minimum MIB of the function E(i) that satisfies a condition DE(i−1)<0 and DE(i)>0;

determining a position of the innermost boundary of the blood vessel as the value of $E_i$ corresponding to a local maximum of the second derivative DDE(i) within a region between the coordinates of the MIB and FIB; and determining a position of the outermost boundary of the blood vessel within a region starting from a global minimum of the first derivative DE(i) where index i changes from FIB towards the end of the function DE(i), the outermost boundary position being a maximum of the second derivative DDE(i) within this region.

23. The method according to claim 13 and further comprising the step of calculating a blood flow in the blood vessel as a function of its blood vessel diameter and blood flow velocity therein.

24. The method according to claim 13 and further comprising the step of calculating the vascular elasticity index of the blood vessel according to the relationship:

$$\frac{D_s - D_d}{D_d}$$

where $D_s$ is the blood vessel diameter at peak systole and $D_d$ is the blood vessel diameter at diastole.

25. The method according to claim 14 and further comprising the steps of:

determining the blood flow velocity profile across the diameter of the blood vessel; and calculating shear rate at the outermost surface $S_O$ and the innermost surface $S_I$ of the blood vessel's wall relative to the ultrasound transducer according to the relationship:

$$\frac{dV}{dD} \text{ at } D = 0, \text{ and } D.$$

26. The method according to claim 13 and further comprising the steps of:

measuring time dependent arterial blood pressure Pr(t); and calculating a time dependent distal resistance index Rs(t) according to the relationship:

$$Rs(t) = \frac{Pr(t)}{F(t)}$$

where is F(t) is the instantaneous blood flow.

27. The method according to claim 14 further comprising the steps of utilizing the determined chord lengths of the two beams to automatically determine the center of the chord, thereby enabling automatic representation of a blood flow velocity waveform.

28. The method according to claim 27, wherein innermost and outermost vessel boundaries are determined from the n-element vector $E_i$ for each of the beams, and the gate coordinate for the center of the blood vessel is determined as a mean position between the innermost and outermost boundaries.

* * * * *